United States Patent [19]

McPherson

[11] Patent Number: 5,535,735
[45] Date of Patent: Jul. 16, 1996

[54] SIMULATED CIGARETTE INHALER

[76] Inventor: Andrew McPherson, 118-15 180 St., Saint Albans, N.Y. 11434

[21] Appl. No.: 408,496

[22] Filed: Mar. 22, 1995

[51] Int. Cl.⁶ ................................................ A61M 15/06
[52] U.S. Cl. .................................... 128/202.21; 131/273
[58] Field of Search ................. 128/202.21, 200.23, 128/203.23, 203.11; 131/273, 360

[56] References Cited

U.S. PATENT DOCUMENTS

| | | | |
|---|---|---|---|
| 4,393,884 | 7/1983 | Jacobs | 131/273 |
| 4,945,929 | 8/1990 | Egilmex | 131/273 |
| 4,945,931 | 8/1990 | Gori | 131/335 |

FOREIGN PATENT DOCUMENTS

| | | | |
|---|---|---|---|
| 2665639 | 2/1992 | France | 128/202.21 |

*Primary Examiner*—Edgar S. Burr
*Assistant Examiner*—Eric P. Raciti

[57] ABSTRACT

An inhaler for simulating a cigarette and supplying oxygen to an individual. The inventive device includes a pressurized supply assembly for containing a pressurized gas such as oxygen. A valve assembly extends from the pressurized supply assembly for dispensing the pressurized gas through a mouthpiece in response to inhalation so as to simulate the operation of a cigarette.

1 Claim, 3 Drawing Sheets

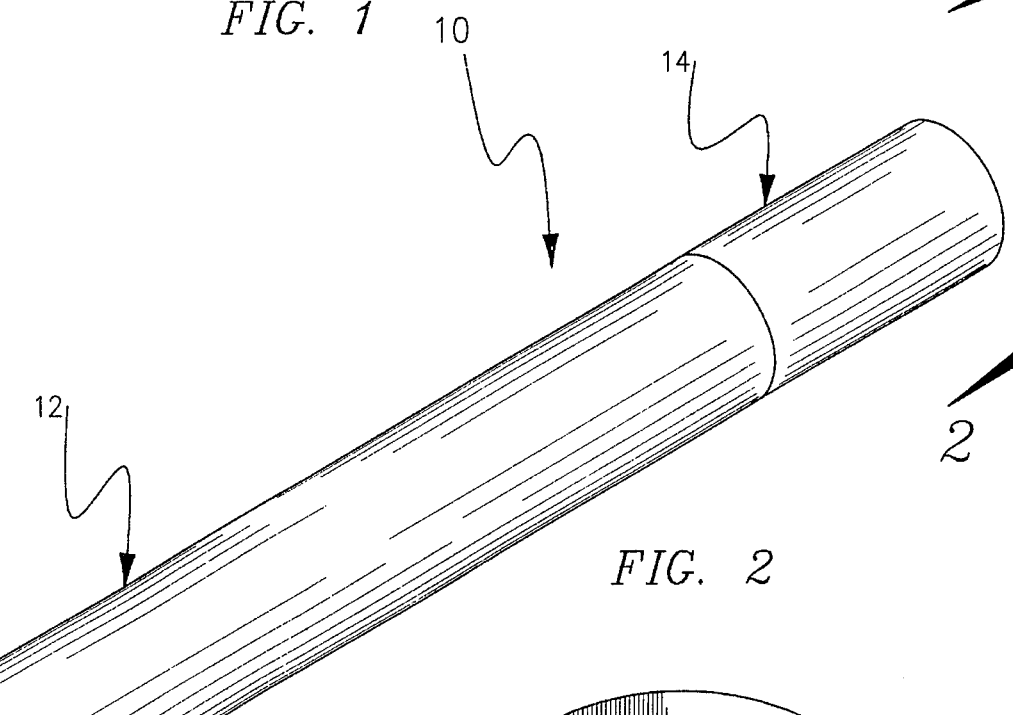
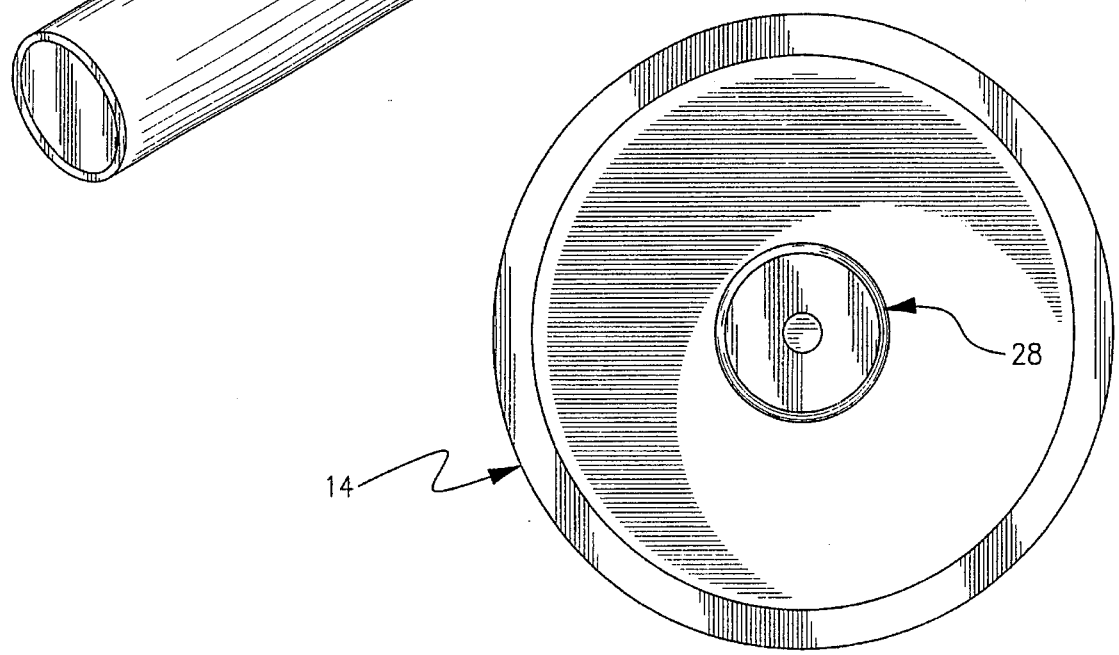
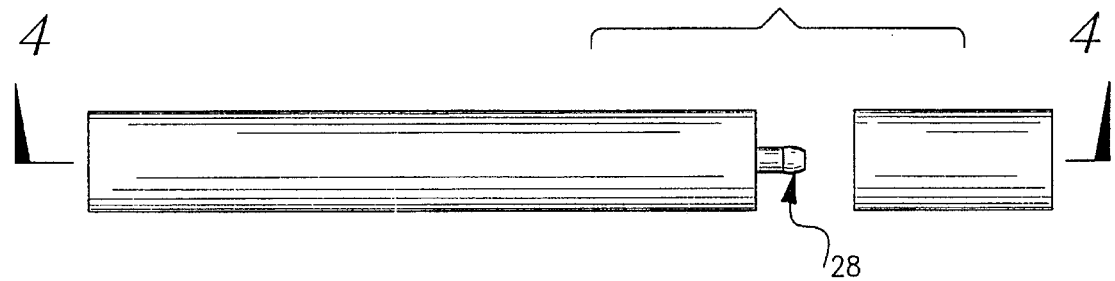

SIMULATED CIGARETTE INHALER

BACKGROUND OF THE INVENTION

1. Field of the Invention

The present invention relates to respiratory gas supply devices and more particularly pertains to a simulated cigarette inhaler for simulating a cigarette and supplying oxygen to an individual.

2. Description of the Prior Art

The use of respiratory gas supply devices is known in the prior art. More specifically, respiratory gas supply devices heretofore devised and utilized are known to consist basically of familiar, expected and obvious structural configurations, notwithstanding the myriad of designs encompassed by the crowded prior art which have been developed for the fulfillment of countless objectives and requirements.

Known prior art respiratory gas supply devices include U.S. Pat. No. 3,521,643,; U.S. Pat. No. 3,631,856; U.S. Pat. No. 4,083,372; U.S. Pat. No. 5,042,510; U.S. Pat. No. 5,080,115; and U.S. Pat. No. 5,190,060.

While these devices fulfill their respective, particular objectives and requirements, the aforementioned patents do not disclose a simulated cigarette inhaler for simulating a cigarette and supplying oxygen to an individual which includes a pressurized supply means for containing a pressurized gas such as oxygen, and a valve means extending from the pressurized supply means for dispensing the pressurized gas through a mouthpiece in response to inhalation so as to simulate the operation of a cigarette.

In these respects, the simulated cigarette inhaler according to the present invention substantially departs from the conventional concepts and designs of the prior art, and in so doing provides an apparatus primarily developed for the purpose of simulating a cigarette and supplying oxygen to an individual.

SUMMARY OF THE INVENTION

In view of the foregoing disadvantages inherent in the known types of respiratory gas supply devices now present in the prior art, the present invention provides a new simulated cigarette inhaler construction wherein the same can be utilized for dispensing oxygen to an individual in response to inhalation. As such, the general purpose of the present invention, which will be described subsequently in greater detail, is to provide a new simulated cigarette inhaler apparatus and method which has many of the advantages of the respiratory gas supply devices mentioned heretofore and many novel features that result in a simulated cigarette inhaler which is not anticipated, rendered obvious, suggested, or even implied by any of the prior art respiratory gas supply devices, either alone or in any combination thereof.

To attain this, the present invention generally comprises an inhaler for simulating a cigarette and supplying oxygen to an individual. The inventive device includes a pressurized supply assembly for containing a pressurized gas such as oxygen. A valve assembly extends from the pressurized supply assembly for dispensing the pressurized gas through a mouthpiece in response to inhalation so as to simulate the operation of a cigarette.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new simulated cigarette inhaler apparatus and method which has many of the advantages of the respiratory gas supply devices mentioned heretofore and many novel features that result in a simulated cigarette inhaler which is not anticipated, rendered obvious, suggested, or even implied by any of the prior art respiratory gas supply devices, either alone or in any combination thereof.

It is another object of the present invention to provide a new simulated cigarette inhaler which may be easily and efficiently manufactured and marketed. as oxygen, and a valve means extending from the pressurized supply means for dispensing the pressurized gas through a mouthpiece in response to inhalation so as to simulate the operation of a cigarette.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

It is a further object of the present invention to provide a new simulated cigarette inhaler which is of a durable and reliable construction.

An even further object of the present invention is to provide a new simulated cigarette inhaler which is susceptible of a low cost of manufacture with regard to both materials and labor, and which accordingly is then susceptible of low prices of sale to the consuming public, thereby making such simulated cigarette inhalers economically available to the buying public.

Still yet another object of the present invention is to provide a new simulated cigarette inhaler which provides in the apparatuses and methods of the prior art some of the advantages thereof, while simultaneously overcoming some of the disadvantages normally associated therewith.

Still another object of the present invention is to provide a new simulated cigarette inhaler for simulating a cigarette and supplying oxygen to an individual in response to inhalation.

Yet another object of the present invention is to provide a new simulated cigarette inhaler which includes a pressurized supply means for containing a pressurized gas such

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is an isometric illustration of a simulated cigarette inhaler according to the present invention.

FIG. 2 is an end elevation view of the invention taken from line 2—2 of FIG. 1.

FIG. 3 is an exploded side elevation view of the present invention.

DESCRIPTION OF THE PREFERRED EMBODIMENT

Figure 4:
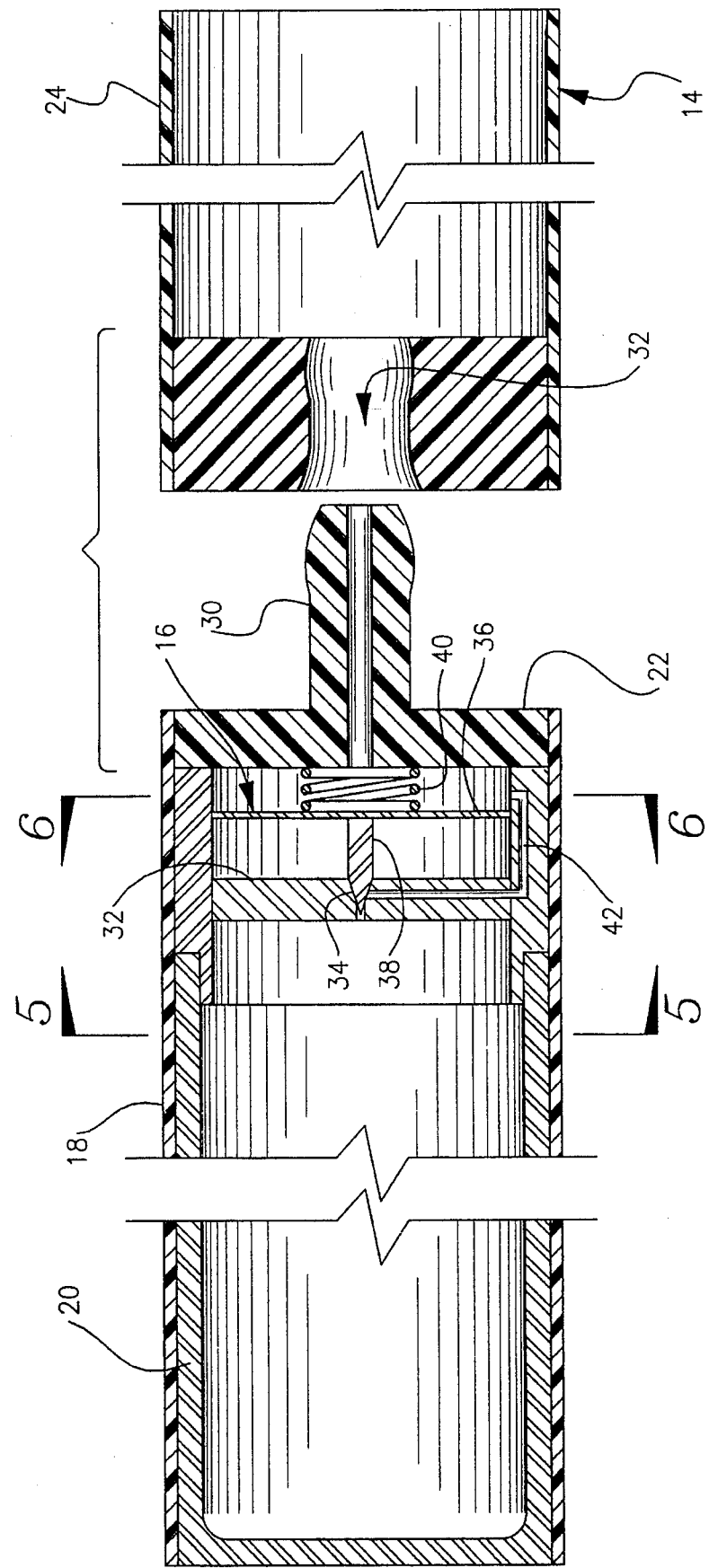
FIG. 4 is a cross sectional view taken along line 4—4 of FIG. 3.

With reference now to the drawings, and in particular to FIGS. 1–6 thereof, a new simulated cigarette inhaler embodying the principles and concepts of the present invention and generally designated by the reference numeral 10 will be described.

More specifically, it will be noted that the simulated cigarette inhaler 10 comprises a pressurized supply means 12 for containing a pressurized gas such as oxygen or the like and for simulating a major portion of a cigarette. A mouthpiece 14 is removably coupled to the pressurized supply means 12 and is shaped so as to resemble a minor portion of a cigarette. As shown in FIG. 4, a valve means 16 is interposed between the mouthpiece 14 and the pressurized supply means 12 for dispensing a pressurized gas from the pressurized supply means 12 in response to a vacuum created within the mouthpiece 14 by an individual during inhalation. By this structure, an individual conditioned or having the habit of smoking can instead inhale a pressurized gas such as oxygen in lieu of smoking a conventional cigarette.

As best illustrated in FIGS. 2 through 4, it can be shown that the pressurized supply means 12 according to the present invention 10 preferably comprises a substantially cylindrical outer casing 18 shaped so as to resemble a major portion of an unillustrated cigarette. A pressure cylinder 20 is removably positioned within the outer casing 18 and is preferably frictionally retained therein such that the pressure cylinder 20 can be selectively separated from the outer casing 18 as desired by an end user. The pressure cylinder 20 is closed at a first end thereof and includes a pressure cylinder end wall 22 disposed at a second end thereof. By this structure, a pressurized gas such as oxygen or the like can be positioned within the pressure cylinder 20 for containment thereof until dispensed by the valve means 16 in a manner which will subsequently be described in more detail.

The mouthpiece 14 preferably comprises a mouthpiece cylinder 24 open at a first end for positioning into fluid communication with an individual's mouth, and including a mouthpiece end wall 26 extending across a second end thereof. A coupling means 28, as shown in FIGS. 2 through 4, is provided with the present invention 10 for removably coupling the mouthpiece 14 to the pressure cylinder end wall 22 of the pressurized supply means 12. To this end, the coupling means 28, as shown in FIG. 4, preferably comprises a hollow projection 30 extending from the pressure cylinder end wall 22 and into fluid communication with an interior of the pressure cylinder 20. The mouthpiece end wall 26 is shaped so as to define a receiving bore 32 cooperatively shaped relative to the hollow projection 30 such that the hollow projection can be snap-fitted into the receiving bore 32 so as to retain the mouthpiece 14 relative to the pressurized supply means 12. By this structure, the mouthpiece 14 can be selectively separated from the pressurized supply means 12, whereby the placement of the pressure cylinder 20 relative to the outer casing 18 can be easily accomplished.

Figure 5:
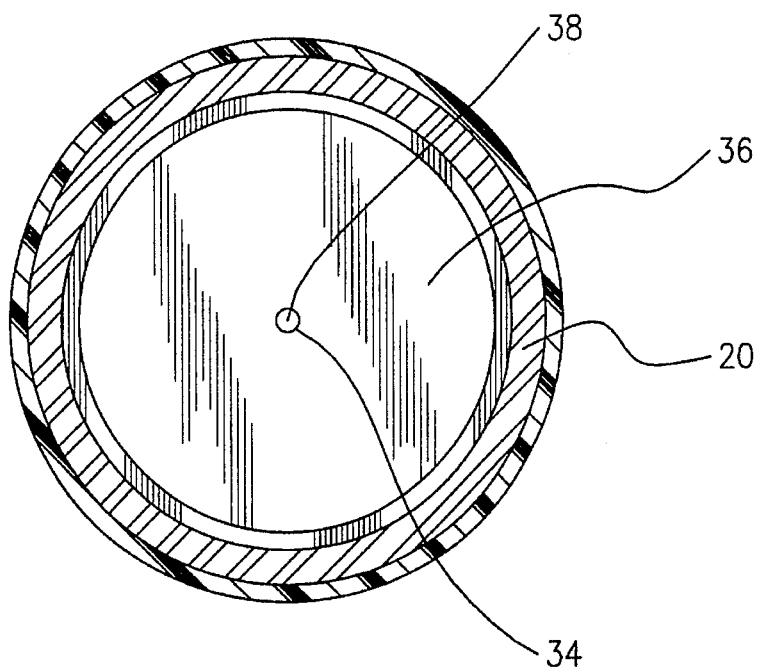
FIG. 5 is a cross sectional view taken along line 5—5 of FIG. 4.
Figure 6:
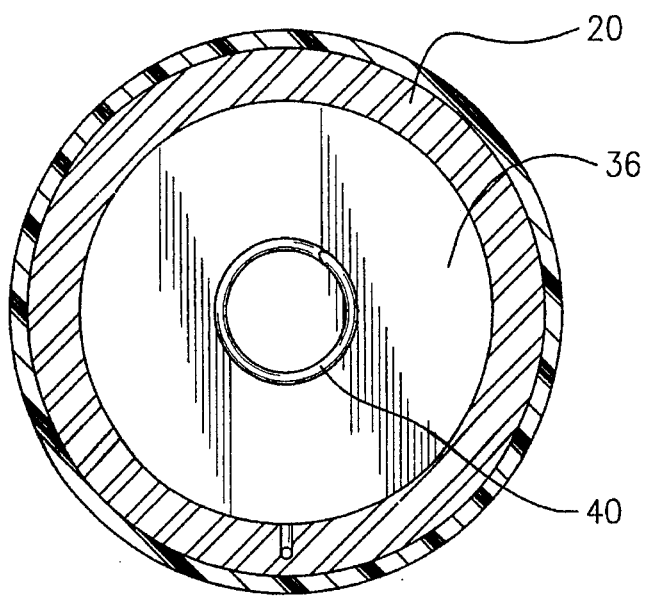
FIG. 6 is a cross sectional view taken along line 6—6 of FIG. 4.

If desired, the valve means 16 may comprise valves known within the prior art. Specifically, U.S. Pat. No. 5,099,837, U.S. Pat. No. 5,042,473, U.S. Pat. No. 4,971,108, and U.S. Pat. No. 4,744,356 all disclose inhalation responsive valves which can be utilized as the valve means 16 of the present invention 10 and are all herein incorporated by reference. However, the preferable valve means 16 for use with the present invention 10 is illustrated in FIGS. 4 through 6, and it can be shown that the same comprises a valve plate 32 extending across an interior of the pressure cylinder 20. The valve plate 32 is shaped so as to define a valve seat 34 directed therethrough. A diaphragm 36 is mounted across an interior of the pressure cylinder 20 between the valve plate 32 and the pressure cylinder end wall 22, as shown in FIG. 4 of the drawings. A needle valve 38 is mounted to the diaphragm 36 and positioned so as to normally engage the valve seat 34. A spring 40 is interposed between the diaphragm 36 and the pressure cylinder end wall 22 so as to bias the needle valve 38 into the valve seat 34 to maintain the valve means 16 in a normally closed configuration. A by-pass line 42 extends into fluid communication with the valve seat 34 and the hollow projection 30. By this structure, a vacuum created within the mouthpiece 14 will bias the flexible diaphragm 36 towards the pressure cylinder end wall 22 so as to remove the needle valve 38 from the valve seat 34. Pressurized gas within the pressure cylinder 20 will then flow through the by-pass line 42 for egress through the hollow projection 30 and into an individual inhaling. Further, a blocking of the pressurized gas from egress through the hollow projection 30 will result in a return of the diaphragm 36 to the normal position illustrated in FIG. 4 so as to position the needle valve 38 back into the valve seat 34 to terminate flow of pressurized gas from the pressure cylinder 20.

In use, the simulated cigarette inhaler 10 according to the present invention can be easily utilized by an individual to effect dispensing of a beneficial respiratory gas such as oxygen as a substitute for habitual cigarette smoking. The present invention 10 allows for replacement of the pressure cylinder 20 as desired so as to permit refilling of the invention when needed.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A simulated cigarette inhaler comprising:

a pressurized supply means comprising a substantially cylindrical outer casing shaped to resemble a major portion of a cigarette; a pressure cylinder removeably positioned within the outer casing, the pressure cylinder being closed at a first end thereof and including a pressure cylinder end wall disposed at a second end thereof;

a mouthpiece removeably coupled to the pressurized supply means and shaped to resemble a minor portion of a cigarette, said mouthpiece comprising a mouthpiece cylinder open at a first end for positioning into fluid communication with an individual's mouth, and including a mouthpiece end wall extending across a second end thereto; and further comprising a coupling means having a hollow projection extending from said pressure cylinder end wall at said second end thereof into fluid communication with an interior of the pressure cylinder, the mouthpiece end wall being shaped so as to define a receiving bore cooperatively shaped relative to the hollow projection such that the hollow projection can be snap-fitted into the receiving bore to retain the mouthpiece relative to the pressurized supply means; and a valve means interposed between the mouthpiece and the pressurized supply means and communicating though the pressure cylinder end wall at the second end thereof for dispensing a pressurized gas from said supply means in response to a vacuum created within the mouthpiece by an individual during inhalation, said valve means comprising a valve plate extending across an interior of the pressure cylinder, the valve plate being shaped so as to define a valve seat directed therethrough; a diaphragm mounted across an interior of the pressure cylinder between the valve plate and the pressure cylinder end wall; a needle valve mounted to the diaphragm and positioned so as to normally engage the valve seat; a spring interposed between the diaphragm and the pressure cylinder end wall so as to bias the needle valve into the valve seat to maintain the valve means in a normally closed configuration; and a by-pass line extending into fluid communication with the valve seat and the hollow projection.

* * * * *